(12) United States Patent
Kery et al.

(10) Patent No.: US 9,907,540 B2
(45) Date of Patent: Mar. 6, 2018

(54) TISSUE LIQUID DETECTION SYSTEM

(75) Inventors: Robert Kery, Castle Cove (AU); John Gal, Castlecrag (AU); Sung-Wei Chen, Las Vegas, NV (US); Christopher J Rothfuss, legal representative, Laramie, WY (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 157 days.

(21) Appl. No.: 14/362,907

(22) PCT Filed: Jun. 11, 2012

(86) PCT No.: PCT/AU2012/000659
§ 371 (c)(1),
(2), (4) Date: Jun. 4, 2014

(87) PCT Pub. No.: WO2013/185162
PCT Pub. Date: Dec. 19, 2013

(65) Prior Publication Data
US 2014/0316273 A1    Oct. 23, 2014

(51) Int. Cl.
*A61B 8/08*    (2006.01)
*A61B 5/00*    (2006.01)
*A61B 5/05*    (2006.01)

(52) U.S. Cl.
CPC .......... *A61B 8/5223* (2013.01); *A61B 5/0095* (2013.01); *A61B 5/0507* (2013.01);
(Continued)

(58) Field of Classification Search
CPC ... A61B 8/5223; A61B 8/5292; A61B 5/0507; A61B 8/0858; A61B 8/48; A61B 8/085;
(Continued)

(56) References Cited

U.S. PATENT DOCUMENTS 5,553,618 A * 9/1996 Suzuki ..................... A61N 7/02
                                                    600/411
5,713,356 A * 2/1998 Kruger ................. A61B 5/0091
                                                    600/407

(Continued)

OTHER PUBLICATIONS

"Photoacoustic tomography," Wikipedia, accessed at http://en.wikipedia.org/wiki/Photoacoustic_tomography, last modified on Dec. 14, 2011, pp. 1-2.
(Continued)

*Primary Examiner* — Peter Luong
(74) *Attorney, Agent, or Firm* — Maschoff Brennan

(57) ABSTRACT

A method of detecting liquid in animal tissue is disclosed. The method comprises providing an electromagnetic radiation generator, and applying electromagnetic radiation to a tissue region using the electromagnetic radiation generator. The characteristics of the electromagnetic radiation are selected so as to cause differential heating in a tissue region based on liquid content in the tissue region, differential expansion of matter in the tissue region, and thereby generation of ultrasound signals that vary according to the liquid content. The method also comprises providing an ultrasound detector, detecting the ultrasound signals using the ultrasound detector, and using the detected ultrasound signals to produce an indication of concentration of liquid in the tissue region and a determination as to whether a change in liquid concentration in the tissue region has occurred.

20 Claims, 2 Drawing Sheets

(52) U.S. Cl.
CPC .......... *A61B 5/4848* (2013.01); *A61B 8/0858* (2013.01); *A61B 8/5292* (2013.01); *A61B 5/4255* (2013.01); *A61B 5/4875* (2013.01); *A61B 8/085* (2013.01); *A61B 8/48* (2013.01)

(58) Field of Classification Search
CPC ... A61B 5/4848; A61B 5/0095; A61B 5/4875; A61B 5/4255
See application file for complete search history.

(56) References Cited

U.S. PATENT DOCUMENTS

| | | | | |
|---|---|---|---|---|
| 6,463,336 | B1* | 10/2002 | Mawhinney | A61N 1/40 600/14 |
| 7,122,012 | B2 | 10/2006 | Bouton et al. | |
| 2002/0035327 | A1 | 3/2002 | Kruger | |
| 2004/0236234 | A1* | 11/2004 | Fuchs | A61B 8/06 600/500 |
| 2007/0016032 | A1* | 1/2007 | Aknine | A61B 5/0048 600/437 |
| 2007/0299341 | A1 | 12/2007 | Wang et al. | |

OTHER PUBLICATIONS

"Thermoacoustic imaging," Wikipedia, accessed at http://web.archive.org/web/20100807081750/http://en.wikipedia.org/wiki/Thermoacoustic_imaging, last modified on Mar. 11, 2010, pp. 1-8.

Balderramoa et al., "Current management of billiary complications after liver transplantation: Emphasis on endoscopic therapy,"Gastroenterologia y Hepatologia, vol. 34, No. 2, pp. 107-115 (2011).

Essani, R. et al., "Anastomotic Leak in colorectal surgery: a review," astroenterologia Polska/Gastroenterology, vol. 16, No. 2, pp. 123-127 (2009).

Hyman, N.,et al., "Anastomotic Leaks After Intestinal Anastomosis: It's Later Than You Think," Annanls of Surgery, vol. 245, No. 2, pp. 254-258 (2007).

Kruger, et al., "Thermoacoustic CT with Radio Waves: A medical Imaging Paradigm," Radiology, vol. 211, No. 1, pp. 275-278, (1999).

Ku et al., "Thermoacoustic and Photoacoustic Tomography of Thick Biological Tissues Toward Breast Imaging,"Technology in Cancer Research & Treatment, vol. 4, No. 5, pp. 559-566 (2005).

Mckinaly et al., "Review of the Scientific Evidence for Limiting Exposure to Electromagnetic Fields (3-300 Ghz)," Documents of the NRPB: vol. 15, No. 3, pp. 223 (2004).

Schepps J. L. and Foster K.R.,"The UHF and mocrowave dielectric properties of normal and tumor tissues," Phys. MED. Bio., vol. 25, No. 6, pp. 1149-1159(1980).

Semenov S., "Microwave omograpy: review of the progress towards clinical applications," Phil. Trans.R. Soc. A, vol. 367, pp. 3021-3042, The Royal Society (2009).

Vorst et al., "RF/Microwave interaction with Biological Tissue," IEEE Press, Chapter 3, pp. 93-152 (2006).

Zhang et al., "Pathogenesis and treatment to postoperative bile leakage: report of 38 cases," Hepatobillary Pancreat Dis int, vol. 4, No. 3, pp. 441-444(2005).

International Search Report for PCT/AU2012/000659 dated Aug. 21, 2012.

Lin et al., "Detection of Abdominal Abscesses After Colorectal Surgery: Ultrasonography, Computed Tomography and Gallium Scan" Colorectal Cancer: Methods of Cancer Diagnosis, Therapy and Prognosis 4, I(2): 119-135 (2009).

\* cited by examiner

TISSUE LIQUID DETECTION SYSTEM

CROSS-REFERENCE TO RELATED APPLICATION

The present Application claims priority to and the benefit as a National Stage Application under 35 U.S.C. § 371 of International Application No. PCT/AU2012/000659, filed on Jun. 11, 2012, the entire disclosures of which is incorporated herein by reference for any and all purposes in its entirety as if fully set forth herein.

BACKGROUND

Unless otherwise indicated herein, the materials described in this section are not prior art to the claims in this application and are not admitted to be prior art by inclusion in this section.

In the medical field, post-operative leakage can present a significant risk to patients to the extent that undetected leakage can cause serious short and/or long term consequences to patient health. For example, leakage from colorectal anastomosis can cause death if left undetected.

Existing procedures for detecting liquid and/or liquid leakages are prone to false negatives and tend to be expensive and/or are invasive for the patient.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

A liquid detection system for detecting liquid in tissue and a method of detecting liquid is generally described. An example system for detecting liquid in animal tissue includes an electromagnetic radiation generator arranged to apply electromagnetic radiation to a tissue region. The characteristics of the electromagnetic radiation are selected to cause differential heating in the tissue region based on liquid content in the tissue region and thereby differential expansion of matter in the region. Expansion of matter in the tissue region causes ultrasound signals to be created and an ultrasound detector detects the ultrasound signals. The system uses the detected ultrasound signals to produce an indication of concentration of liquid in the tissue region and a determination as to whether a change in liquid concentration in the tissue region has occurred.

DETAILED DESCRIPTION

Figure 1:
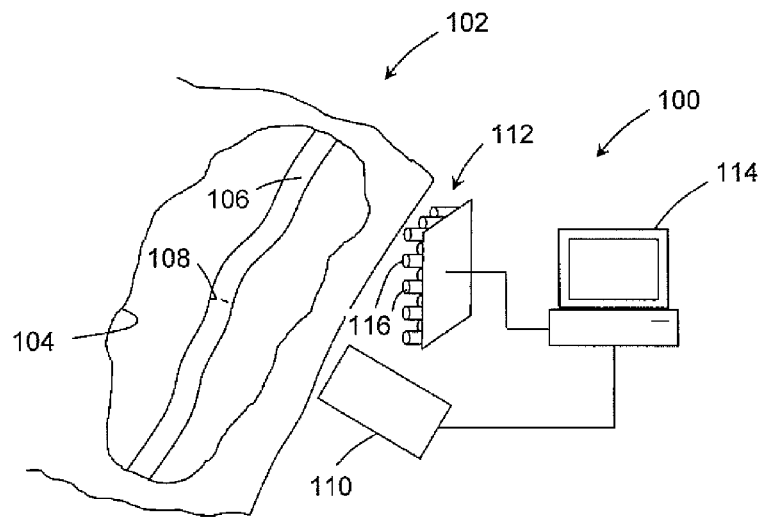
FIG. 1 is a diagrammatic representation of an example of a detection system for detecting liquid in animal tissue.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, and devices related to detecting liquid in an animal.

Briefly stated, a detection system for detecting liquid in animal tissue is generally disclosed.

An embodiment of the detection system makes use of the thermo-acoustic effect. According to the thermo-acoustic effect, irradiation of a selected body with electromagnetic energy of appropriate frequency and power causes the temperature of the body to rise, and as a consequence the body expands. The mechanical expansion produces an acoustic wave that propagates outward.

Without wishing to be bound by theory, it is believed that the thermo-acoustic effect can be used to detect differences in liquid content across a tissue region at a spatial resolution less than about 1 mm. The energy absorption of tissue is determined by its Linear Absorption Coefficient (LAC). For soft tissue with relatively small differences in water bound fractions between 0.74 and 0.92, the corresponding LAC values are between 0.39 and 0.70. This suggests that a relatively small change in water content provides an appreciable change in LAC and therefore an appreciable change in ultrasound signals generated as a result of absorptive heating.

FIG. 1 is a diagrammatic representation of an example of a detection system 100 for detecting liquid in a tissue region 102 of an animal and that is arranged according to at least some embodiments described herein.

The example detection system 100 is shown in FIG. 1 during use adjacent a tissue region 102 of a patient animal, typically a human. The tissue region 102 in this example is an anastomosis region of a human, for example a colorectal anastomosis region. With this type of anastomosis, detection of liquid leakage from the anastomosis is very important because leakage of liquid from a tissue junction can cause serious patient health consequences, including death.

FIG. 1 includes a cut-away portion 104 so that anastomosis tissue 106 having a tissue junction 108 can be seen.

The system 100 includes an electromagnetic radiation generator, in this example an electromagnetic pulse generator 110 configured to generate electromagnetic pulses that are absorbed in different amounts by tissue and liquid present in the tissue region 102. In some embodiments, the electromagnetic radiation generator 110 is configured to generate electromagnetic signals that are absorbed in different amounts by tissue and liquid present in the tissue region 102. As a consequence of the differing absorption amounts in the liquid and tissue, different amounts of energy are converted to heat, and therefore areas in the tissue region that have a higher concentration of liquid will expand more than areas that have a lower concentration of liquid. This, in turn, causes areas in the tissue region that have a higher concentration of liquid to generate ultrasound signals of greater intensity than areas that have a lower concentration of liquid. The system 100 also includes an ultrasound detector 112 configured to detect ultrasound signals emanating from the tissue region 102 in response to the generated electromagnetic radiation, and an analyzer 114 configured to analyze the detected ultrasound signals and make determinations as to the liquid present in the tissue region 102, in particular whether a change in liquid concentration has occurred in the tissue region 102 using the detected ultrasound signals.

In the present embodiment, the electromagnetic signals include microwave pulses of wavelength, frequency and power selected so as to cause regions of higher liquid concentration in the tissue region 102 to expand more than regions of lower liquid concentration. In some embodiments, the microwave pulses have a duration between about 0.5 µs and about 2 µs, a peak power between 25 kW and 50 kW, and a pulse repetition rate between about 50 Hz and about 4 kHz. In some embodiments, the frequency of the microwave pulses is selected so as to provide the maximum absorption differential between liquid and other tissue whilst providing good depth penetration, for example 434 MHz. Such a favourable absorption differential between liquid and tissue is achieved, for example, when the electromagnetic signals are in the microwave and near infra-red regions of the electromagnetic spectrum.

In some embodiments, the microwave pulses have an average power between about 0.75 W and about 60 W.

Without wishing to be bound by theory, the inventors believe that a pulse energy of about 15-20 mJ will be sufficient to provide a contrast ratio of 3:1 at a depth of 15 cm. In this regard, it should be noted that the pulse energy does not determine the average power because the average power is also dependent on the pulse repetition rate. For a pulse energy of about 15-20 mJ, duration 1 µs, and pulse repetition rate 1000, the average power is about 15 W.

However, it will be understood that liquid in the tissue region 102 may be caused to be heated using other types of electromagnetic radiation. In some embodiments, the electromagnetic signals may include laser generated pulses, for example near infra-red light pulses, for example with a near infra-red laser at frequency 1064 nm, with pulse durations of 5-10 nm and pulse repetition rate of 10-20 Hz. In a further alternative embodiment, the electromagnetic radiation includes RF signals.

It will be understood that the characteristics of the electromagnetic pulses are selected such that the tissue is exposed to safe levels of electromagnetic energy whilst still achieving sufficient localized heating to produce detectible ultrasound signals. This may be achieved by generating pulses of very short duration, for example about 0.5 µs, relatively high peak power of 25 KW, and relatively low average power <60 W. Since the average power is dependent on the pulse repetition rate, the average power can be readily modified by modifying the pulse frequency.

In accordance with the thermo-acoustic effect, rapid heating of liquid in the tissue region 102 causes heating and relatively rapid expansion of the liquid-containing tissue region according to the relative amount of liquid in the tissue region 102. This, in turn, causes generation of ultrasound pulses that are indicative of the amount and location of liquid in the tissue region 102.

In some embodiments, the pulse generator 110 is configured to direct microwave pulses towards a region covering the tissue region 102, and in this example to direct the microwave pulses towards a volume approximately 10 cm$^3$ with a centroid approximately coinciding with the tissue junction 108.

In order to increase the likelihood that the generated electromagnetic pulses are directed towards the tissue junction 108 and surrounding tissue, and that the ultrasound detector is disposed at a repeatable location for each reading, a patient's body may be provided with alignment or fiducial marks. In some embodiments, multiple readings may be taken by disposing the pulse generator and/or the ultrasound detector 112 at multiple locations relative to the tissue junction 108, and therefore in some embodiments multiple alignment marks may be provided for this purpose. Correct alignment may also be achieved by imaging the tissue, for example using ultrasound, magnetic resonance or X-rays, and using the produced images to align the electromagnetic pulse generator and/or the ultrasound detector. In the present embodiment, the ultrasound detector 112 includes an array of ultrasound transducers 116, each ultrasound transducer 116 configured to detect ultrasound signals generated in response to heating induced in the tissue region 102. In some embodiments, the analyzer 114 is configured to make determinations as to whether the liquid concentration in the tissue region has changed, for example because a leakage of liquid may have occurred, by comparing the detected ultrasound signals with reference ultrasound signals representative of previous readings taken of the same patient and/or representative of readings taken from a similar tissue region of another patient. In the present embodiment, the ultrasound readings taken from the array of ultrasound transducers 116 are used to produce 3 dimensional electromagnetic energy absorption profiles. The absorption profiles are indicative of the amount of electromagnetic energy absorbed at locations across the tissue region, the amount of heat produced as a result of the absorption, and the distribution of liquid present at locations across the tissue region.

The analyzer 114 may be controlled so as to focus on a particular tissue location by calculating the time delay and phase of a received ultrasound pulse.

In one embodiment, the 3D profiles may be produced using a 2D transducer array that is steered to produce many directed receive orientations. For each transmit pulse, a parallel processing system produces several image points, the locations of which in the image correspond to the tangents of the angles of the receive orientations in the azimuth and elevation planes. The brightness of each image point is the weighted integral of the echo data received along each receive path.

In some embodiments, the analyzer 114 is also arranged to make determinations as to whether a change in liquid distribution, such as a leakage of liquid, may have occurred in the tissue region using the produced energy absorption profiles together with relevant biometric data, including temperature, age, body weight, location of tissue region, and so on.

In an example, the analyzer 114 calculates a liquid content value by averaging the ultrasound signals from the transducers 116 in the array of transducers, and compares the liquid content value with one or more stored reference liquid content values. Each of the liquid content values is indicative of the relative liquid content in a tissue region.

In the present embodiment, the analyzer 114 is implemented using a computing device, in this example a personal computer, and associated software. However, it will be understood that other implementations are envisaged. In some embodiments, the software includes neural network software.

In an implementation using a neural network, an initial database of case histories is required in order to train the network. The database can be built by recording the liquid content values throughout the recovery cycle for a range of cases covering diverse biometric data. The values are then rated, for example as normal or abnormal, based on the final outcome for the patient. For example, for an anastomosis patient, if after the recovery period the patient is found to not have had a serious leak then the liquid content values recorded would all be rated as 'normal'. However, if the patient has had a leak, the readings would be reviewed by an expert and those readings indicated by the expert as having liquid levels above the normal range rated as 'abnormal'.

It is anticipated that this initial database could be created over a few months and the neural network initially trained. The database would then be supplemented with new data through normal use.

Figure 2:
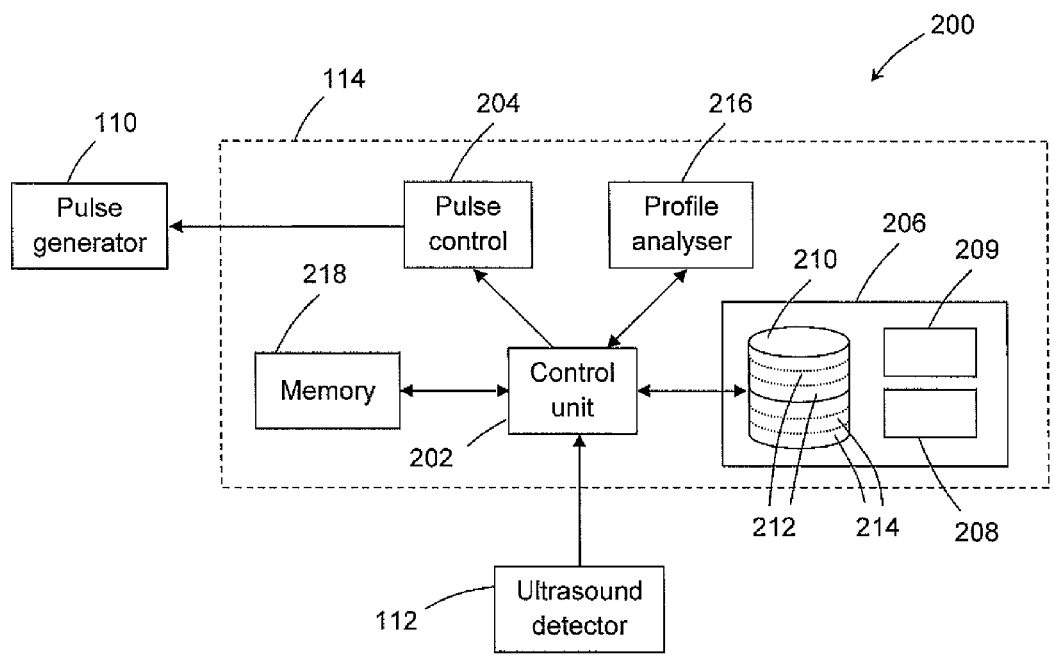
FIG. 2 is a diagram illustrating example functional components of the system shown in FIG. 1.

FIG. 2 is a diagram illustrating functional components 200 of the system 100 shown in FIG. 1. The functional components 200 include a control unit 202 arranged to control and coordinate operations in the analyzer 114, a pulse control device 204 arranged to control the pulse generator 102 according to instructions received from the control unit 202 so that the pulse generator 102 produces pulses of desired frequency, duration and power to effect heating of liquid in the tissue region.

The functional components 200 also include a data storage device 206 arranged to store programs 208 for use by the control unit 202 to control and coordinate operation of the analyzer 114, and to store data usable by the analyzer 114 to make determinations as to whether a leakage of liquid may have occurred in the tissue region. In some embodiments, at least part of the data is stored in a database 210 configured to store patient reference records 212 indicative of previously determined absorption data including previously determined liquid content values and previously determined energy absorption profiles for a particular patient, and global reference records 214 indicative of absorption data including previously determined liquid content values and previously determined energy absorption profiles for other patients. The data storage device 206 is also arranged to store biometric data 209, for example for use in determining whether an abnormal amount of liquid exists in a tissue region of interest. Biometric data may include temperature, age, body weight, sex, location of any surgical procedures (and the outcome), and location of the tissue region. Biometric data may also include any part or whole of a patient's medical file.

The functional components 200 also include a profile analyzer 216 configured to use liquid content values and/or one or more energy absorption profiles obtained from a patient, liquid content values and/or energy absorption profiles stored in the database 210, and/or the biometric data 209 to make a determination regarding the tissue area, such as whether an abnormal amount of liquid exists in the tissue area. In some embodiments, the profile analyzer 216 may include neural network and/or expert system software to analyze the liquid content values and/or produced absorption profiles and determine whether the profiles are indicative of a change in liquid concentration in the tissue region 102. The functional components 200 also include a memory 218 used to temporarily store programs and data during implementation of the system.

It will be understood that in this embodiment the control unit 202, the pulse control device 204, and the profile analyzer 216 are implemented by a personal computer using one of, or a combination of software stored in the data storage device 206, or additional hardware operating to perform any necessary specialized operations. The profile analyzer 216 may be either a personal computer or a specific purpose built computer system, either of which incorporate the appropriate logic circuits or software simulation (or both) for performing the operations of one or more neural network(s). However, it will be understood that other implementations are envisaged, including hardware implementations, and hardware and software implementations.

In an example, microwave pulses of pulse width between about 0.5 μs and 1 μs, frequency between about 50 Hz and 4 kHz, and average power between about 0.75 W and 60 W, are generated by the electromagnetic radiation generator 110 and directed towards the tissue junction 108 and surrounding tissue. The generated microwave pulses cause liquid in the tissue region to heat more rapidly than other matter in the tissue region. As a consequence, the areas of the tissue region that contain the most liquid heat up more and therefore experience more tissue expansion and generate more ultrasound signals than areas that contain less liquid. It follows, therefore, that by analyzing the ultrasound signals produced in response to the microwave pulses, it is possible to make a determination as to the distribution of liquid in the tissue region and, for example, whether the excitable liquid distribution is normal or abnormal.

In a particular example, colorectal anastomosis surgery has been carried out on a human patient and it is necessary to monitor whether leakage of intestinal liquid has occurred from the anastomosis for a period of time after the surgery until it is determined that leakage is no longer likely to occur.

With this example, after surgery or as part of the surgery process, alignment marks are provided on the patient's skin or fiduciary markers are provided on or beneath the patient's skin at locations that facilitate repeated correct alignment of the electromagnetic radiation generator 110 and ultrasound detector 112 relative to the anastomosis tissue region. At periodic intervals after the surgery, for example daily, microwave pulses suitable to effect heating of liquid in the tissue region are generated and directed towards the tissue region 102. The patient may be required to fast, and in particular to drink minimal liquid, immediately prior to taking a reading, and/or to consume water about 2 hours before taking a reading. This may maximize the likelihood that liquid due to a leak would be present and detectible in the tissue region.

In this example, the microwave pulses may have a pulse energy about 12.5 mJ, and this results in a 7:1 signal to noise contrast between tissues of relative liquid content 0.75 and 0.85 at a depth of 6 cm. The ultrasound signals produced in response to generation of the microwave pulses are detected by the ultrasound transducers 116 and after each application of microwave pulses, a microwave absorption profile is produced that is indicative of the amount and locations of liquid present in the tissue region 102.

The microwave absorption profile in this example is used to produce a liquid content value by averaging ultrasound intensity values derived from the transducers 116 in the transducer array.

Liquid content values are taken prior to surgery so that one or more reference liquid content values particular to the patient are obtained for comparison purposes with liquid content values taken after surgery.

A reference liquid content value taken prior to surgery is used to generate an expected time-phased recovery profile for the patient. The recovery profile for a patient defines the expected change in the liquid content value over time after the surgery. For example, for anastomosis, the recovery profile is a curve that starts at a baseline defined by the reference liquid content value, then increases to a peak value after surgery due to an increased level of liquid adjacent the anastomosis, and declines gradually back to the baseline value over a period of up to 30 days. The recovery profile may be tailored to a particular patient by selecting the recovery profile of a previous patient with similar biometric data (such as weight and age) to the present patient and using the current baseline indicator value to calibrate the values on the curve.

The liquid content value generated after each reading is compared with the expected liquid content value suggested by the recovery profile for the patient, and if the liquid content value is greater than the expected liquid content value by more than a defined tolerance, an alert is generated. The alert may be indicative that a leakage of liquid has occurred from the colorectal anastomosis tissue junction 108.

While the system 10 may be used to monitor whether leakage of intestinal liquid has occurred from anastomosis tissue, it will be understood that other applications are envisaged. For example, the system may be used to monitor the presence and/or change of liquid concentrations for other reasons, such as oedema, as a result of trauma such as hematoma, diseases wherein liquid buildup tends to occur, hydrocephaly, internal bleeding, and so on.

Figure 3:
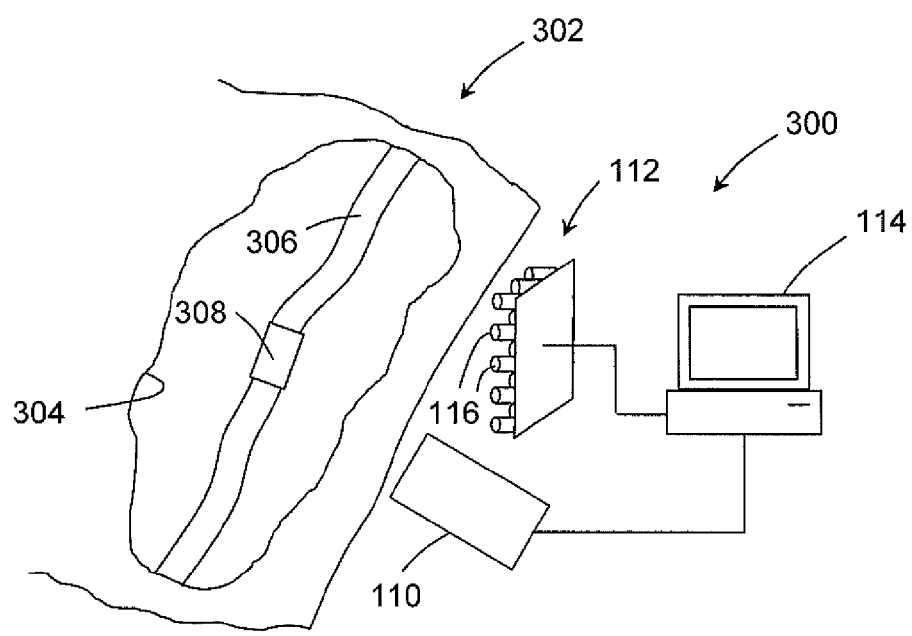
FIG. 3 is a diagrammatic representation of another example of a detection system for detecting liquid in animal tissue.

FIG. 3 is a diagrammatic representation of another example of a detection system 300 for detecting liquid in animal tissue.

The detection system 300 is similar to the example detection system 100 shown in FIGS. 1 and 2, in that a pulse generator 110 is configured to focus microwave pulses in a tissue region 302 including anastomosis tissue 306. In this example, however, an activated collar 308 is disposed around a tissue junction during surgery. The activated collar 308 includes relatively strong electromagnetic energy absorbing material so that when a reading is taken the activated collar 308 will appear as a hot spot in the energy absorption profile, thereby identifying the location of the tissue junction. If a leak occurs from the tissue junction, the leakage would tend to cause a degradation of ultrasound signals from the collar since the leaked liquid would absorb some of the energy of the incident pulses.

In some embodiments, the activated collar includes relatively strong microwave absorbing material, such as iron oxide particles, and may be formed as a flexible biodegradable sheet that is wrapped around the anastomosis tissue junction during surgery.

Figure 4:
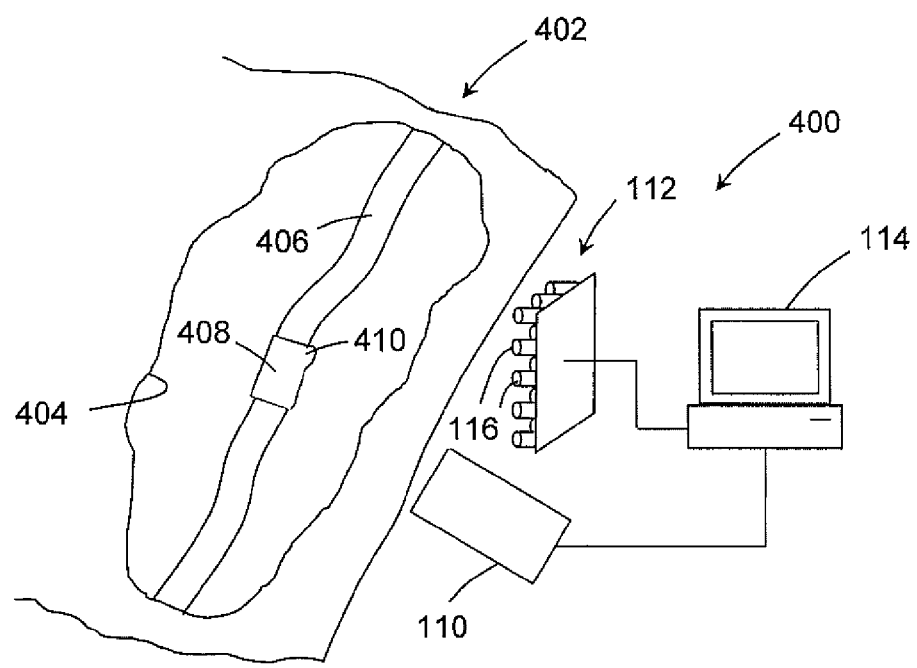
FIG. 4 is a diagrammatic representation of another example of a detection system for detecting liquid in animal tissue.

FIG. 4 is a diagrammatic representation of another example of a detection system 400 for detecting liquid in animal tissue.

The detection system 400 is similar to the example detection system 100 shown in FIGS. 1 and 2, in that a pulse generator 110 is configured to focus microwave pulses in a tissue region 402 including anastomosis tissue 406. In this example, however, an expandable collar 408 is disposed around a tissue junction during surgery. The expandable collar 408 may be formed of biodegradable, flexible, relatively impermeable material that is wrapped around the anastomosis join during surgery. If a leak occurs from the tissue junction, the leaked liquid is localized in the region defined by the collar 408 and the collar 408 expands at a portion 410 of the collar adjacent the leakage. The collar 408 may include relatively strong electromagnetic energy absorbing material so that the collar 408, and in particular changes to the collar that occur as a result of leakages, can be more easily detected.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of detecting a liquid in an animal tissue, the method comprising:
applying electromagnetic radiation to a tissue region using an electromagnetic radiation generator, wherein characteristics of the electromagnetic radiation are selected so as to cause differential heating in the tissue region based on liquid content in the tissue region, thereby causing differential expansion of matter in the tissue region and generation of ultrasound signals that vary according to the liquid content in the tissue region;
providing an ultrasound detector;
detecting the generated ultrasound signals using the ultrasound detector;
using the detected ultrasound signals to determine a liquid content value in the tissue region based on ultrasound pulses generated in response to expansion of the tissue region, wherein the expansion of the tissue region is based on the differential heating of the liquid in the tissue region, and to determine whether a change in liquid concentration in the tissue region has occurred based on a comparison of the detected ultrasound signals with reference ultrasound signals; and
determining whether the liquid content value is abnormal based on a comparison of the liquid content value to stored values of expected liquid content.

2. The method as claimed in claim 1, wherein the electromagnetic radiation generator comprises a microwave, near infra-red, or RF signal generator.

3. The method as claimed in claim 1, wherein the electromagnetic radiation generator comprises an electromagnetic pulse generator arranged to generate electromagnetic pulses, wherein the electromagnetic pulses comprise microwave pulses.

4. The method as claimed in claim 3, wherein applying the electromagnetic radiation comprises applying the microwave pulses of duration substantially in the range 0.5 µs to 2 µs.

5. The method as claimed in claim 4, wherein applying the microwave pulses comprises applying the microwave pulses of average power substantially in the range 0.75 W to 60 W.

6. The method as claimed in claim 5, wherein applying the microwave pulses comprises applying the microwave pulses of frequency substantially in the range 50 Hz to 4 kHz.

7. The method as claimed in claim 1, wherein using the detected ultrasound signals comprises using the detected ultrasound signals to produce an absorption profile indicative of absorption of electromagnetic energy in the tissue region, and comparing the absorption profile with a previously generated reference absorption profile and using the comparison to determine whether the absorption profile is indicative of the change in liquid concentration in the tissue region.

8. The method as claimed in claim 1, wherein using the detected ultrasound signals comprises using the detected ultrasound signals to produce the liquid content value indicative of an average detected ultrasound intensity, and comparing the liquid content value with a reference recovery profile for a patient, and wherein the reference recovery profile defines the expected change in the liquid content value over time.

9. The method as claimed in claim 8, further comprises selecting the reference recovery profile using biometric data associated with the animal tissue, wherein the biometric data includes at least one of temperature, body weight, age, and location of the tissue region.

10. The method as claimed in claim 1, further comprising disposing liquid absorptive material adjacent to the tissue region and determining whether the absorption profile is indicative of the change in the liquid concentration in the tissue region based on a detected liquid content value in the liquid absorptive material.

11. A method of detecting an anastomotic leakage in a patient, the method comprising:
applying electromagnetic radiation to an anastomosis tissue region using an electromagnetic radiation generator, wherein characteristics of the electromagnetic radiation are selected so as to cause differential heating in the tissue region based on liquid content in the tissue region, thereby causing expansion of matter in the tissue region and generation of ultrasound signals that vary according to the liquid content in the tissue region;
providing an ultrasound detector;
detecting the generated ultrasound signals using the ultrasound detector;
using the detected ultrasound signals to determine a liquid content value in the tissue region based on ultrasound pulses generated in response to expansion of the tissue region, wherein the expansion of the tissue region is based on the differential heating of the liquid in the tissue region, and to determine whether a leakage of the liquid from the anastomosis tissue region has occurred based on a comparison of the detected ultrasound signals with reference ultrasound signals; and
determining whether the liquid content value is abnormal based on a comparison of the liquid content value to stored values of expected liquid content.

12. The method as claimed in claim 11, wherein the anastomosis tissue is colorectal anastomosis tissue.

13. A system for detecting a liquid in an animal tissue, the system comprising:
an electromagnetic radiation generator arranged to apply electromagnetic radiation to a tissue region, wherein characteristics of the electromagnetic radiation selected so as to cause differential heating in a tissue region based on liquid content in the tissue region, thereby causing expansion of matter in the tissue region and generation of ultrasound signals that vary according to the liquid content in the tissue region;
an ultrasound detector arranged to detect the ultrasound signals;
the system further comprising an analyzer arranged to:
use the detected ultrasound signals to determine a liquid content value in the tissue region based on ultrasound pulses generated in response to expansion of the tissue region, wherein the expansion of the tissue region is based on the differential heating of the liquid in the tissue region;
determine whether a leakage of the liquid from the anastomosis tissue region has occurred based on a comparison of the detected ultrasound signals with reference ultrasound signals; and
determine whether the liquid content value is abnormal based on a comparison of the liquid content value to stored values of expected liquid content.

14. The system as claimed in claim 13, wherein the electromagnetic radiation generator is arranged to generate microwave, near infra-red, or RF signals.

15. The system as claimed in claim 13, wherein the electromagnetic radiation comprises microwave radiation.

16. The system as claimed in claim 15, wherein the microwave radiation comprises microwave pulses of duration substantially in the range 0.5 µs to 2 µs.

17. The system as claimed in claim 16, wherein the microwave pulses comprise an average power substantially in the range 0.75 W to 60 W.

18. The system as claimed in claim 13, wherein the electromagnetic radiation comprises frequency of pulses substantially in the range 50 Hz to 4 kHz.

19. The system as claimed in claim 13, wherein the analyzer is configured to use the detected ultrasound signals to produce the liquid content value indicative of an average detected ultrasound intensity and compare the liquid content value with a reference recovery profile for a patient, wherein the reference recovery profile defines the expected change in the liquid content value over time, and wherein the analyzer is configured to use biometric data associated with the patient to select the reference recovery profile, and wherein the biometric data includes temperature, age, body weight and/or location of the tissue region.

20. The system as claimed in claim 13, further comprises a liquid absorptive material to be disposed adjacent to the tissue region, the analyzer arranged to determine whether an absorption profile is indicative of a change in liquid concentration in the tissue region based on a detected liquid content value in the liquid absorptive material.

* * * * *

UNITED STATES PATENT AND TRADEMARK OFFICE
CERTIFICATE OF CORRECTION

PATENT NO. : 9,907,540 B2  
APPLICATION NO. : 14/362907  
DATED : March 6, 2018  
INVENTOR(S) : Kery et al.

It is certified that error appears in the above-identified patent and that said Letters Patent is hereby corrected as shown below:

In the Specification

In Column 5, Line 20, delete "generator 102" and insert -- generator 110 --, therefor.

In Column 5, Line 21, delete "generator 102" and insert -- generator 110 --, therefor.

In Column 8, Line 31, delete "recitation no" and insert -- recitation, no --, therefor.

In Column 8, Line 53, delete "general such" and insert -- general, such --, therefor.

In Column 8, Line 60, delete "general such" and insert -- general, such --, therefor.

In the Claims

In Column 9, Line 53, in Claim 1, delete "to expansion" and insert -- to the expansion --, therefor.

In Column 11, Line 7, in Claim 13, delete "radiation selected" and insert -- radiation are selected --, therefor.

In Column 12, Line 22, in Claim 19, delete "weight" and insert -- weight, --, therefor.

Signed and Sealed this  
Twenty-sixth Day of June, 2018

Andrei Iancu  
*Director of the United States Patent and Trademark Office*